(12) United States Patent
Merced-O'Neill et al.

(10) Patent No.: US 12,232,733 B2
(45) Date of Patent: Feb. 25, 2025

(54) CONNECTOR AND WRAP FOR END-TO-SIDE NERVE COAPTATION

(71) Applicant: Axogen Corporation, Alachua, FL (US)

(72) Inventors: Orlando Merced-O'Neill, Bandera, TX (US); Michael Raymond Orrico, Gainesville, FL (US)

(73) Assignee: Axogen Corporation, Alachua, FL (US)

( * ) Notice: Subject to any disclaimer, the term of this patent is extended or adjusted under 35 U.S.C. 154(b) by 933 days.

(21) Appl. No.: 17/063,240

(22) Filed: Oct. 5, 2020

(65) Prior Publication Data

US 2021/0068837 A1 Mar. 11, 2021

Related U.S. Application Data

(63) Continuation of application No. 15/344,908, filed on Nov. 7, 2016, now Pat. No. 10,835,253.

(60) Provisional application No. 62/251,901, filed on Nov. 6, 2015.

(51) Int. Cl.
*A61B 17/11* (2006.01)
*A61B 17/00* (2006.01)
*A61L 27/16* (2006.01)
*A61L 27/18* (2006.01)
(Continued)

(52) U.S. Cl.
CPC .......... *A61B 17/1128* (2013.01); *A61L 27/16* (2013.01); *A61L 27/18* (2013.01); *A61L 27/3604* (2013.01); *A61L 27/3675* (2013.01); *A61L 27/56* (2013.01);
(Continued)

(58) Field of Classification Search
CPC ...... A61B 17/1128; A61B 2017/00902; A61B 2017/1132; A61B 2017/1135; A61B 2017/111; A61B 5/6877; A61L 27/16; A61L 27/18; A61L 27/3604; A61L 27/3675; A61L 27/56; A61L 2430/32;
(Continued)

(56) References Cited

U.S. PATENT DOCUMENTS 4,778,467 A * 10/1988 Stensaas .................. A61F 2/04
606/152
4,920,962 A 5/1990 Proulx
5,147,399 A 9/1992 Dellon et al.
(Continued)

FOREIGN PATENT DOCUMENTS

JP  2002-501777 A  1/2002
JP  2002-518082 A  6/2002
(Continued)

OTHER PUBLICATIONS

Extended European Search Report issued in EP Application No. 16863151.3 on Jul. 2, 2019.

*Primary Examiner* — Jocelin C Tanner
(74) *Attorney, Agent, or Firm* — Bookoff McAndrews, PLLC

(57) ABSTRACT

The problem of attaching a donor nerve stump to a recipient nerve for an end-to-side coaptation is solved by the use of a tissue connector. The tissue connector can have a body for receiving the donor nerve stump and one or more overflaps for attaching the tissue connector with the donor nerve stump therein to the epineurium on the side of the recipient nerve. Sutures can also be used to secure the tissue connector and nerves in place.

36 Claims, 4 Drawing Sheets

(51) Int. Cl.
*A61L 27/36* (2006.01)
*A61L 27/56* (2006.01)

(52) U.S. Cl.
CPC .............. *A61B 2017/00902* (2013.01); *A61B 2017/1132* (2013.01); *A61B 2017/1135* (2013.01); *A61L 2430/32* (2013.01)

(58) Field of Classification Search
CPC ........ A61L 27/383; C08L 23/06; C08L 71/02; A61F 2/064
See application file for complete search history.

(56) References Cited

U.S. PATENT DOCUMENTS

| | | | |
|---|---|---|---|
| 5,643,340 A * | 7/1997 | Nunokawa | A61F 2/064 623/1.49 |
| 6,090,117 A | 7/2000 | Shimizu | |
| 6,110,188 A * | 8/2000 | Narciso, Jr. | A61B 17/11 606/153 |
| 6,179,848 B1 * | 1/2001 | Solem | A61B 17/11 606/153 |
| 6,740,101 B2 | 5/2004 | Houser et al. | |
| 6,743,243 B1 * | 6/2004 | Roy | A61B 17/11 606/155 |
| 7,285,235 B2 * | 10/2007 | Rapacki | B29C 41/14 264/154 |
| 7,615,373 B2 * | 11/2009 | Simpson | A61L 27/3839 623/23.72 |
| 8,337,394 B2 | 12/2012 | Vakharia | |
| 2002/0013591 A1 * | 1/2002 | Fleischman | A61F 2/064 606/155 |
| 2006/0079952 A1 * | 4/2006 | Kaplan | A61F 2/97 623/1.11 |
| 2007/0219610 A1 * | 9/2007 | Israel | A61F 2/82 623/1.11 |
| 2008/0195124 A1 | 8/2008 | Borghi | |
| 2009/0105733 A1 | 4/2009 | Coleman et al. | |
| 2010/0010517 A1 * | 1/2010 | Stopek | A61B 17/1114 606/153 |
| 2011/0152898 A1 * | 6/2011 | Kochevar | A61B 17/1128 606/152 |
| 2014/0094932 A1 | 4/2014 | Deister et al. | |
| 2014/0336681 A1 | 11/2014 | Agarwal et al. | |
| 2014/0379009 A1 | 12/2014 | Yu et al. | |
| 2015/0086605 A1 * | 3/2015 | Mauney | B29C 39/003 623/23.72 |
| 2015/0313595 A1 | 11/2015 | Houghton et al. | |
| 2017/0224436 A1 * | 8/2017 | Deister | A61L 31/048 |

FOREIGN PATENT DOCUMENTS

| | | |
|---|---|---|
| JP | 2003-190192 A | 7/2003 |
| JP | 2003-530916 A | 10/2003 |
| JP | 2009-118927 A | 6/2009 |
| JP | 2010-535072 A | 11/2010 |
| KR | 2003-0087196 | 11/2003 |
| WO | WO 92/10975 A1 | 7/1992 |
| WO | WO 2012/133019 A1 | 10/2012 |

* cited by examiner

Secured with interrupted stitches at wrap around and donor nerve

CONNECTOR AND WRAP FOR END-TO-SIDE NERVE COAPTATION

CROSS-REFERENCE TO A RELATED APPLICATION

This application is a continuation of U.S. application Ser. No. 15/344,908, filed on Nov. 7, 2016, which claims the benefit of U.S. Provisional Application No. 62/251,901, filed Nov. 6, 2015, each of which is hereby incorporated by reference in its entirety, including all figures, tables and drawings.

BACKGROUND OF INVENTION

The current gold standard for nerve repair is autologous nerve grafting, particularly in the presence of major loss of nerve tissue; however, there are situations in which this technique may not be feasible, such as when there is a limited amount of available graft tissue, when a proximal nerve stump is not available, when nerve is transected too far from target organ, or when there is excessive morbidity at the donor site. Surgical alternatives have been proposed, such as the use of synthetic and biological tubulization, the application of cultured Schwann cells, and the use of end-to-side neurorrhaphy techniques (M. G. Lykissas, "Current concepts in end-to-side neurorrhaphy," World Journal of Orthopaedics, vol. 2, no. 11, pp. 102-106, 2011.)

The end-to-side neurorrhaphy technique has been known by surgeons for over a hundred years. This technique entails grafting the distal nerve stump of a damaged nerve to the side of a healthy neighboring nerve. This technique can aid in maintaining the integrity and viability of the distal nerve to prevent loss of function and atrophy. There has been increased interest in this technique and numerous recent studies have been conducted in order to further understand the mechanisms of nerve regeneration with this technique and how to improve clinical applications and positive patient results. The end-to-side neurorrhaphy technique is being accepted as a feasible alternative for regaining nerve function when the proximal stump of the donor damaged nerve is not available or injury has occurred too distal to the target organ. The technique has also been used to avoid symptomatic (painful) neuroma formation by grafting a proximal sensory nerve stump into a small branch motor or sensory nerve.

The technique is based on the concept that collateral axonal sprouting from a healthy, local recipient nerve can occur with a distal stump of a donor transected nerve, if the distal stump is sutured in end-to-side fashion to the local recipient nerve. Studies have also shown that it is not necessary to create an epineural window, or opening, in the recipient nerve site to encourage collateral axonal sprouting. However, when the raw or open distal nerve stump is attached to the recipient site, axonal growth may not be limited to the recipient and donor nerves and random axon growth can occur outside the nerves causing a variety of symptoms, including soft tissue attachments and painful neuromas.

The ability to cover and isolate a coaptation site between a recipient nerve and a donor nerve stump can reduce or eliminate undesired axonal growth into surrounding areas. It can also decrease healing time by directing axonal growth towards the preferred nerve regeneration site, instead of into non-target areas. Covering the coaptation site can also provide reinforcement to the area and inhibit separation of the coapted nerves. The use of implant devices to cover and isolate the nerve ends in end-to-end procedures is known. An implant capable of providing the same or similar benefits for end-to-side procedures could make this technique more acceptable by reducing or eliminating undesirable side effects and improving patient outcomes.

BRIEF SUMMARY

The subject invention provides advantageous novel nerve connectors. More particularly, the subject invention provides nerve connectors for facilitating end-to-side nerve repairs. The device and methods of the subject invention can provide improved healing with fewer side effects in patients in need of such treatment. Covering the coaptation site can also provide protection to the repair by detensioning the sutured nerves and preventing avulsion of the repair should sudden tension occur.

The subject invention successfully addresses the above described side effects associated with the end-to-side surgical nerve technique and provides certain attributes and advantages, which can improve nerve repair and increase positive patient outcomes. In particular, the embodiments of the subject invention provide novel and highly effective methods and devices for convenient and effective coaptation of a donor distal nerve stump to the side of a healthy, sufficiently intact neighboring recipient nerve.

One embodiment of the subject invention is a nerve sleeve or tube device that has at least two lateral splits or lateral cut-outs at one end. This provides at least two overlaps, such that the end of the tube resembles something reminiscent to a V- or U-shape or like the mouth of a fish. The nerve stump of a damaged or a healthy donor nerve can be introduced into the end of the tube with the overlaps extending past the nerve stump. The overlaps can be placed around the outside or epineurium of either a living or dead recipient nerve, so that the donor nerve is positioned on the side of the recipient nerve. In some instances, a cut or opening, referred to as an "epineurial window," can be made in the epineurium of the recipient nerve where the donor nerve stump is to be placed and secured by suture or other means such as fibrin derived products or equivalents, to facilitate axonal growth between the nerves. Once the nerve tube is in place, sutures can be used to secure the nerve tube and overlaps on the donor and recipient nerves.

Another embodiment is a nerve wrap device of expandable diameter. One end of the wrap device can have two or more lateral splits or lateral cut-outs, as described above, to create at least two overlaps. With this embodiment, the tube is a wrapped material that can be opened or expanded to be placed around the distal nerve stump, again, with the overlaps extending past the end of the donor nerve stump. The overlaps can be utilized, as described above, to secure the distal nerve stump to the outside or epineurium of a recipient or neighboring nerve.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

DETAILED DISCLOSURE

Figure 1:
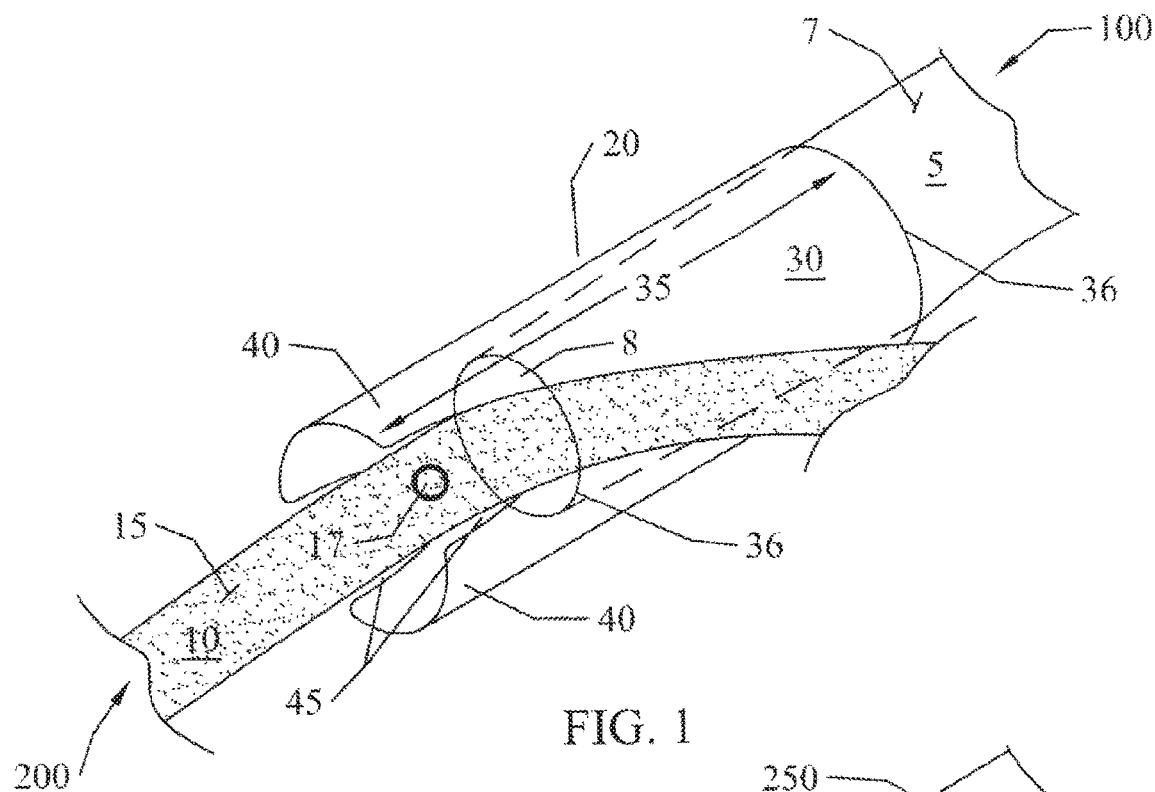
FIG. 1 is an illustration of one embodiment of the subject invention with a donor nerve therein and placed against a recipient nerve.

The subject invention provides an implant useful for coaptation of tissues. More specifically, the subject invention provides nerve connectors, or similar devices, for use in coapting nerves in a patient in need of such treatment. Still more specifically, the embodiments of the subject invention provide nerve connector implants useful for end-to-side nerve coaptation, in particular end-to-side nerve repair procedures.

In the description that follows, a number of terms related to medical devices and nerve repair are utilized. In order to provide a clear and consistent understanding of the specification and claims, including the scope to be given such terms, the following definitions are provided.

The term "patient" as used herein, describes any animal, including mammals, to which the devices and methods of the present invention are applied. Mammalian species that can benefit from the disclosed systems and methods include, but are not limited to, humans, apes, chimpanzees, orangutans, monkeys; domesticated animals (e.g., pets) such as dogs, cats, guinea pigs, hamsters; veterinary uses for large animals such as cattle, horses, goats, sheep; and any wild animal for veterinary or tracking purposes. Human or non-human animal patients can range in age from neonates to elderly.

The term "surgeon" as used here is merely for literary convenience. The term should not be construed as limiting in any way. The devices, apparatuses, methods, techniques and/or procedures of the subject invention could be utilized by any person desiring or needing to do so and having the necessary skill and understanding of the invention.

The terms "nerve" and "nerve tissue" as used herein are merely for literary convenience. Any tissue to which the embodiments of the subject invention can be applied and useful is considered to be encompassed by these terms. By way of non-limiting example, the embodiments of the subject invention could be utilized with vascular or urological tissue, tendons, or muscle tissue.

The term "suture" is also used herein merely for literary convenience. This term should not be construed as limiting in any way. The embodiments of the subject invention could be utilized with any of a variety of devices, substances, and techniques useful for securing and/or connecting tissues, including nerve tissue. This can include, but is not limited to, sutures, staples, vascular clips, hydrogels, fibrins, urethane-based adhesives, and other medical adhesives, or combinations thereof.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Finally, reference is made throughout the application to the "adjoining end" and "insertion end" of the embodiments of the subject invention. As used herein, the adjoining end of the device is that end that is placed closest to, or that can be affixed to, a recipient tissue or nerve. Conversely, the "insertion end" of the device is that end into which the stump of a donor nerve is inserted and is typically but not exclusively furthest away from the adjoining end.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Both natural and synthetic biomaterials can be used to manufacture the devices of the subject invention. In certain embodiments, the biomaterial is a homogenous material. Examples of biomaterials for use in manufacturing the subject invention include, but are not limited to, high density polyethylene (HDPE), polyethylene glycol (PEG) hydrogel, purified proteins from human or animal sources (e.g., membrane of purified collagen or fibrin), cellularized and decellularized tissue constructs (e.g., demineralized bone, small intestine submucosa (SIS), dermis, muscle, fascia, or birth tissue, such as amnion). An HDPE or PEG device can comprise or consist of a cylinder of porous HDPE or PEG surrounded by a layer of non-porous HDPE or PEG. Biomaterials which can form a fluid material, such as soluble purified collagen or particulate SIS and dermis, can be directly cast to form the device without a membrane as an intermediate.

It can be advantageous for embodiments of the subject invention to be flexible and transparent or at least semi-transparent or translucent. In a particular embodiment, small intestine submucosa (SIS) material is utilized. The SIS material can provide sufficient transparency, flexibility, and strength to a nerve connector of the subject invention. During a procedure, a surgeon can usually see the donor nerve stump through the SIS material, which is advantageous for positioning the nerve stump at an appropriate distance from the recipient nerve and aligning the nerve stump with an epineurial window, or opening in the epineurium, if utilized. The flexibility of the material also allows it to be bent or wrapped around the nerve, without breaking or causing damage to the nerve. The SIS material is also amenable for use with sutures for holding it in place once positioned on the nerve.

Reference will be made to the attached Figures on which the same reference numerals are used throughout to indicate the same or similar components. With reference to the attached Figures, which show certain embodiments of the subject invention, it can be seen in FIG. 1 that a nerve connector 20 of the subject invention has an insertion end 100 and an adjoining end 200. In general, a nerve connector includes a body 30 with a lumen 35 therethrough, for receiving a donor nerve stump, and is open to both the adjoining end and insertion end. The adjoining end can further have at least one overlap 40. Alternative embodiments can include two or more overlaps 40 separated by slots 45 into which a recipient nerve can be received. Each of these general components can have one or more subcomponents, which will be discussed in detail below.

Figure 2:
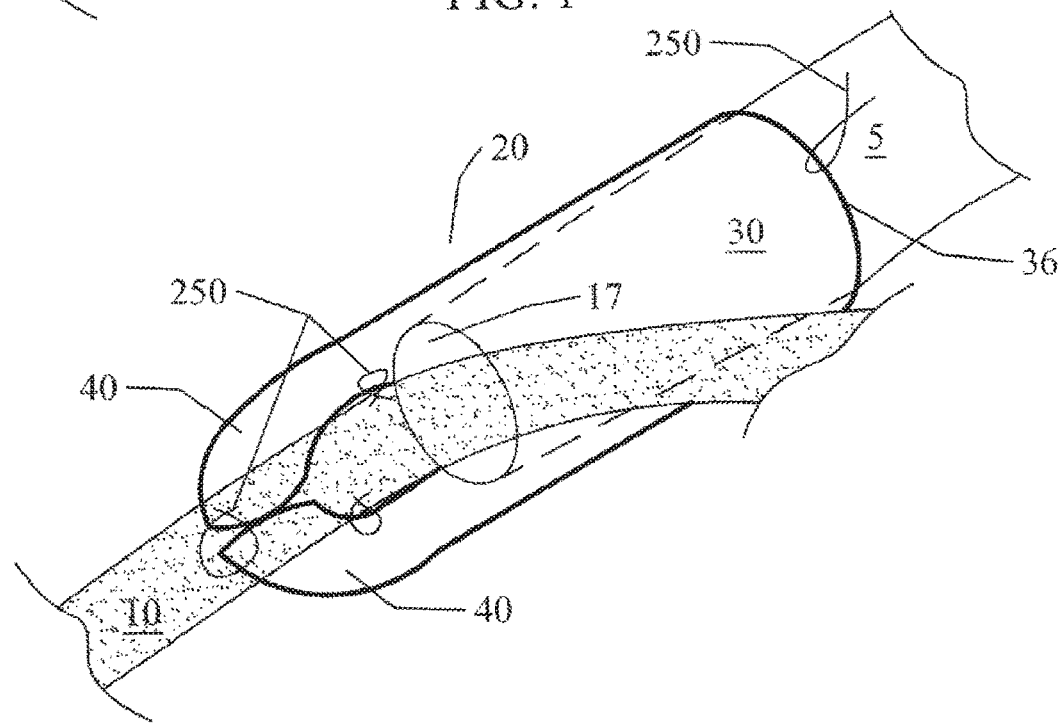
FIG. 2 is an illustration of one embodiment of the subject invention with a donor nerve therein and placed against a recipient nerve, with overlaps secured around the recipient nerve, and secured with sutures.
Figure 3:
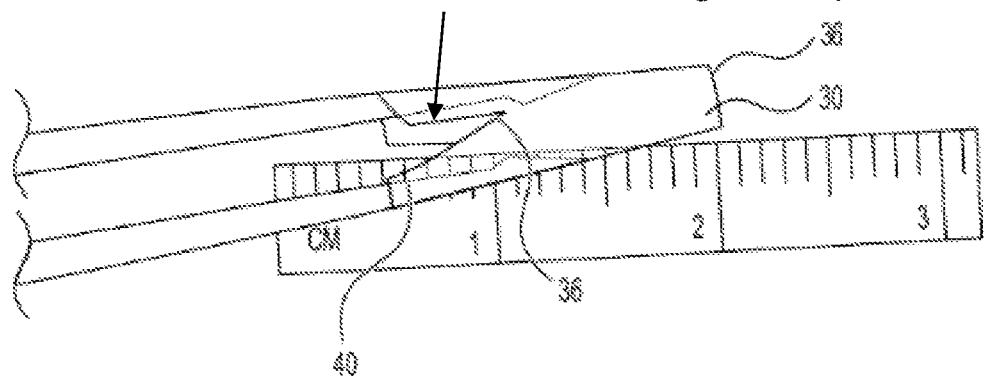
FIG. 3 is an illustration showing one embodiment of a nerve wrap device with overlaps at one end.
Figure 6:
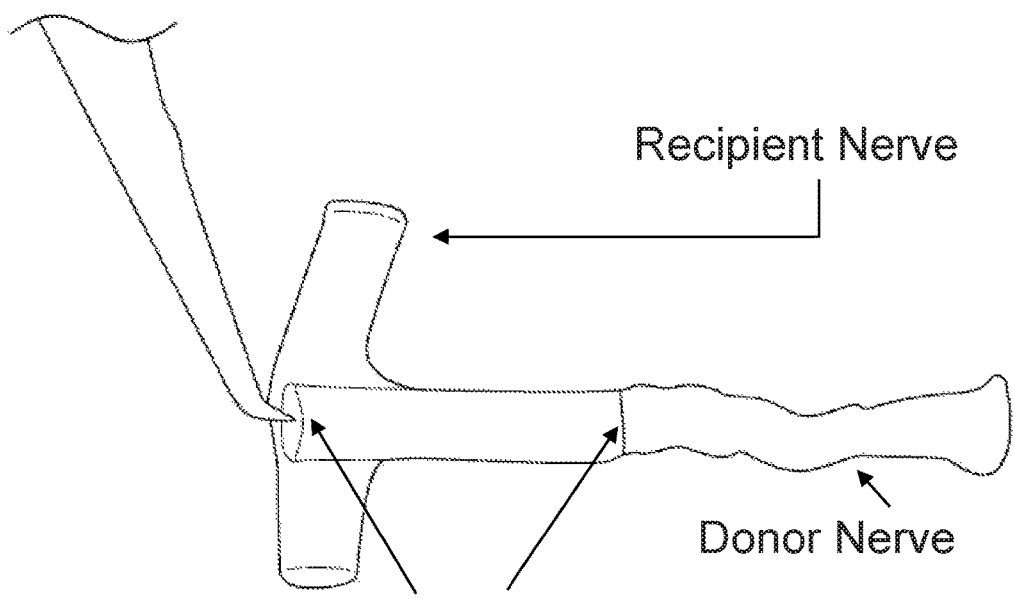
FIG. 6 illustrates how the donor nerve enters the nerve wrap device at the distal end and is brought into close proximity with the recipient nerve, which is situated within the slots on the proximal end of the nerve connector. Also shown is how one or more sutures can be used at strategic locations on the nerve wrap device to secure the donor nerve and the recipient nerve in position with each other. Fibrin glue can also be used to effect nerve attachment or to reinforce suture attachments.

One embodiment of the subject invention has a hollow body 30 that is generally tubular, such that the body is a continuous tubular construct. There can further be a lumen 35 through the longitudinal length of the body with openings 36 at both the insertion end 100 and the adjoining end 200. With this embodiment, a donor nerve stump 5 can be inserted into the insertion end 100 and pushed or pulled towards the adjoining end 200. FIGS. 1, 2, and 6 illustrate examples of a donor nerve within the lumen.

Figure 4A:
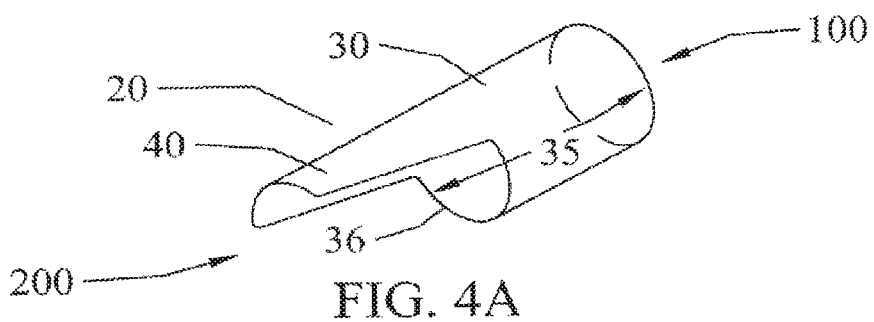
FIGS. 4A-4F show non-limiting examples of different shaped slots that can be used with the embodiments of a nerve wrap device according to the subject invention.

In one embodiment, the diameter of the lumen 35 is generally constant along the length of the continuous body, such that the openings 36 have the same or approximately the same diameter. In an alternative embodiment, shown in FIG. 4D, the diameter of the lumen 35 gradually increases towards the insertion end 100, such that the opening 36 at that end is larger than the opening at the opposite end, which can make inserting the donor nerve stump easier and can allow for an end-to-side connection of nerves having different diameters. The flexibility of the material allows the material around the opening to be pulled, gathered, or crimped around the epineurium 7 of the donor nerve and closed off or secured with sutures 250, if necessary.

Figures 4B, 4C:
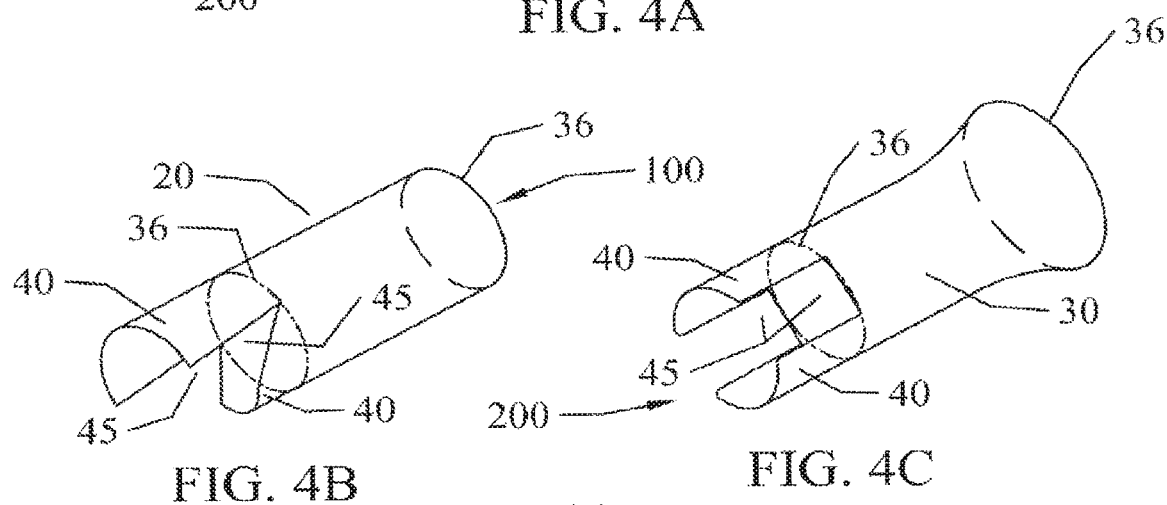
Figures 4D, 4E:
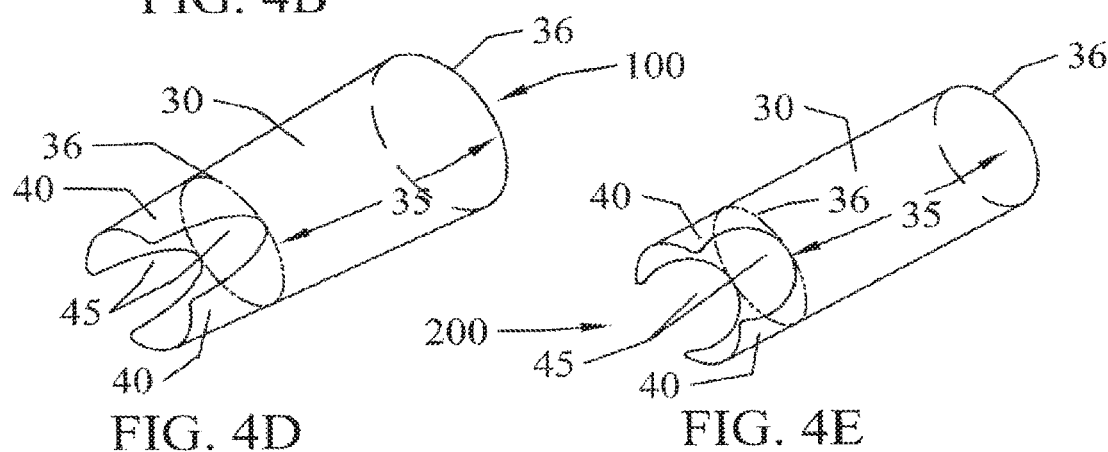

In another embodiment, the diameter of the lumen 35 is substantially consistent along a portion of the body 30 at the adjoining end 200, for example, along at least one half of the length of the body from the adjoining end, and then the body and lumen can flair towards the insertion end 100, as shown, for example, in FIG. 4C. This can make insertion of the donor nerve stump easier at the insertion end and that portion of the lumen that is narrower and is not flaired can aid in holding the nerve stump within the lumen. The flaired opening can be gathered or crimped around the epineurium 7 of the donor nerve and secured with one or more sutures to help hold the nerve connector 20 in place.

Figure 4F:
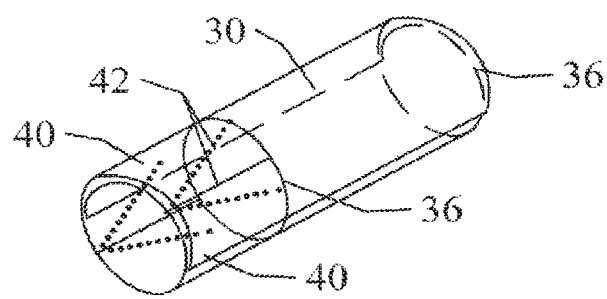

In one embodiment, the body of the device is made by rolling a sheet of biomaterial to form a tubular construct, one example of which is shown in FIG. 4F, where the body of the device is a "roll" of overlapping, or partially overlapping, layers that form a tubular construct of biomaterial, such that the body is a non-continuous tubular construct. The layers of the roll can expand to accommodate nerves, or other tissue, of different diameters. In specific related embodiments, the layers of the rolled biomaterial are overlapped sufficiently to maintain the wall of the tubular construct, when the internal diameter of the device is expanded to accommodate larger diameter nerves.

The length of a body can vary depending upon a variety of factors that are understood by those with skill in the art, including, but not limited to, the length of the donor nerve, the diameter of the donor nerve, the integrity of and/or amount of injury to the donor nerve, where and how many sutures can be used, and the in vivo location of the recipient nerve, as well as other factors. In one embodiment, the length of the body 30 is between approximately 0.5 cm. and approximately 3.0 cm. In a more particular embodiment, the length of the body is between approximately 0.75 cm and approximately 2.0 cm. In a specific embodiment, a body has a length of approximately 1.0 cm.

Likewise, the diameter of the lumen can vary depending upon a variety of factors understood by those with skill in the art, including, but not limited to those factors listed above. In one embodiment, the diameter of the lumen is between approximately 0.25 cm and approximately 0.5 cm. In a more specific embodiment, the diameter of a lumen is approximately 0.3 cm.

At the adjoining end 200, there can be one or more overlaps 40 that are continuous with the body 30 and extend out from, or extend around, the opening at the adjoining end 200 of the body. In one embodiment, there is a single overlap 40, as shown, for example, in FIG. 4A. This embodiment can be useful when only a portion of the recipient nerve epineurium 15 is accessible. With this embodiment, for example, the nerve connector 20 with a donor nerve therein can be brought into proximity to the recipient nerve and the single overlap placed across or around the accessible portion of the recipient nerve epineurium 15 and sutured in place.

Figure 5:
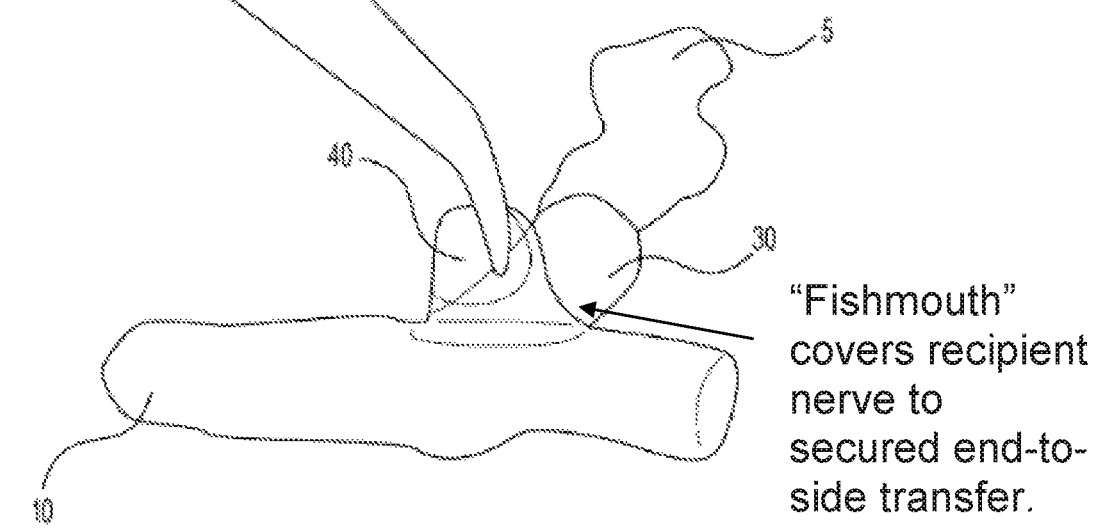
FIG. 5 is an illustration showing one embodiment of a nerve wrap device with the overlaps at one end utilized to attach a donor nerve stump to the side of a recipient neighboring nerve. Also illustrated is the advantageous transparency and flexibility of a nerve wrap device manufactured with small intestine submucosa (SIS) material, which allows easy and visual placement for improved accuracy. Birth tissues, such as, for example, amnion derived products could also be used. Note that in this example the overlap does not wrap all the way around the periphery of the recipient nerve.

FIGS. 3 and 4B through 4E illustrate examples of other embodiments where there are two overlaps 40 that are continuous with the body 30 and extend out from, or extend around, the opening at the adjoining end 200 of the body. With this embodiment, the overlaps can be placed on either side of the epineurium 15 of the recipient nerve 10, such that the overlaps can encircle or at least partially encircle the periphery of the recipient nerve, such as shown, by way of example, in FIGS. 2 and 6. The overlaps can be positioned at or about 180 degrees apart or on approximately opposite sides of the opening, such that they resemble the open mouth of a fish, as demonstrated in FIG. 5. However, this is not a required configuration and in some circumstances it can be beneficial for the overlaps to be offset or not directly opposite to each other around the opening. Further, the overlaps can be of different sizes and/or lengths, an example of which is shown in FIG. 4B.

In an alternative embodiment, there can be more than two overlaps 40. This embodiment can be useful when the recipient nerve 10, or, perhaps, the donor nerve, has an irregular shape or location that makes the use of just two overlaps difficult, inefficient, or ineffective. Multiple overlaps can have the same characteristics and variations as described above for single and two overlap embodiments. A person with skill in the art, having benefit of the subject disclosure, would understand how to incorporate more than two overlaps with a nerve connector 20, according to the subject invention. Thus, examples have not been included in the Figures herein.

The two or more overlaps 40 can have separations 41 therebetween that define the shape or configuration of the overlap. The separation can be any shape or size and creates a point or line at which the overlaps can be separated or spread apart. In one embodiment, a separation is one or more cuts 42 between overlaps, so that they can be separated for placement around or to either side of the recipient nerve, as described above. Typically, a cut is a very narrow separation with minimal or no loss of material between the overlaps. Such a cut can extend from the opening at the adjoining end 200 towards the insertion end 100, an example of which is shown in FIG. 4F. The cut can further be made at an angle relative to the body. For example, the cut 42 can be substantially collinear with the body 30, as shown in FIG. 4F or it can be angled or non-collinear with the body, as exampled by the dotted lines in FIG. 4F.

In one embodiment, the separations between two or more overlaps 40 can be more like slits 45, which are larger and provide more open space, and less material, between the overlaps than a cut. A slit can further have any of a variety of configurations to facilitate placement of the overlaps on or around a recipient nerve 10. The slits can have straight edges, curved edges, or some combination thereof that facilitates attachment or wrapping around a recipient nerve. FIGS. 4B through 4E illustrate a few examples of slits with different shapes that can be employed with the embodiments of the subject invention. Preferably, the length and shape of the slit is such that it can wrap around or over a recipient nerve sufficiently that sutures can be used to secure the overlap. The slit could also be of sufficient length to allow the overlaps to extend completely around the periphery of a recipient nerve such that at least one suture could be used to secure the adjoining ends of the overlaps, as shown, for Example, in FIG. 2.

The length of a slit and conversely the length of the overlaps can vary depending upon any of a variety of factors understood by a person with skill in the art. For example, a connector to be used on sciatic nerve tissue can be larger than a connector intended to be used with nerve tissue in the hand or face. In one embodiment, the length of an overlap is between approximately 0.1 cm. and approximately 4.0 cm. In another embodiment, the length of an overlap is between approximately 0.2 cm. and 2.0 cm. In a more specific embodiment, the length of an overlap is between approximately 0.3 cm. and approximately 0.7 cm. In a specific embodiment, the length of an overlap is approximately 0.5 cm.

Utilization of a tissue connector 20, according to the subject invention, can include installing a donor nerve stump 5 into the lumen, usually by inserting or pushing it into the lumen from the insertion end 100 of the body 30. The terminal end 8 of the donor nerve stump can be brought into proximity to the opening 36 at the adjoining end. It can be advantageous to ensure that there is at least some space between the epineurium of the recipient nerve and the terminal end of the donor nerve. Thus, the terminal end 8 of the donor nerve can be positioned just behind the cuts 42 or slots 45. The one or more overlaps 40 of the tissue connector can then be partially or entirely wrapped around the side of the recipient nerve 10, such that the terminal end 8 of the donor nerve stump 5 is sufficiently close to the side of the recipient nerve to form an end-to-side attachment.

In some situations, a cut or opening, often referred to as an epineurial window 17, can be created in the epineurium 15 of the recipient nerve to encourage or enhance axonal growth between the nerves. As mentioned above, it can be helpful if the material of the tissue connector is transparent or semi-transparent or translucent, allowing a surgeon to see the position of the donor nerve stump within the lumen 35 and so that the position of the donor nerve stump relative to the recipient nerve and/or the epineurial window can be seen as well. This can help the surgeon position the terminal end 8 accurately and ensure that the nerves are not positioned too closely or distorted in shape, before attaching the tissue connector to the nerves with sutures.

Once the terminal end of the donor nerve stump 5 is positioned correctly in relation to the recipient nerve 10, one or more sutures can be used between the donor nerve stump and the tissue connector as well as between the recipient nerve and the one or more overlaps and/or just between the overlaps, if they completely surround the recipient nerve.

Alternatively, the overlaps 40 at the adjoining end 200 can be attached to the recipient nerve and the donor nerve placed within the lumen 35 after the overlaps are attached. This can permit the surgeon to place the opening 36 at the adjoining end 200 in the optimal location on the recipient nerve, ensuring that the terminal end 8 of the donor nerve, when emplaced in the lumen will be properly located as well.

In another alternative, one or some of the overlaps can be attached to the recipient nerve to aid in optimal placement. The donor nerve can then be inserted into the lumen and positioned, such that when the remaining one or more overlaps are attached, the donor nerve is properly placed relative to the recipient nerve. Additional sutures can be used to secure the remaining one or more overlaps and the donor nerve.

The nerve repair technique of attaching a donor nerve stump from a damaged peripheral nerve to the side of a neighboring, usually undamaged, recipient nerve is useful in some cases. Attaching the donor nerve to a recipient nerve can keep the donor nerve viable and ensure that the tissue enervated by the damaged peripheral nerve does not atrophy. Nerve repair devices used for end-to-end nerve repair may not be applicable for end-to-side nerve repairs when a donor nerve stump is attached to the side of a recipient nerve.

The embodiments of the subject invention provide new, biocompatible devices that can make end-to-side nerve repairs easier to perform, inhibit undesirable axonal outgrowth, and provide improved patient outcomes. The tissue connector devices and techniques of the subject invention can help in the attachment of a donor nerve to a recipient nerve and, when formed from appropriate materials, can allow a surgeon to actually see the nerves through the device during placement, for improved accuracy.

The scope of the invention is not limited by the specific examples and suggested procedures and uses related herein since modifications can be made within such scope from the information provided by this specification to those skilled in the art.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

We claim:

1. A tissue connector device for end-to-side connection of tissues, the connector device comprising:
   a hollow body having an insertion end configured to receive a donor tissue end, an adjoining end, and a lumen therebetween; and
   a single overflap extending longitudinally out from the adjoining end of the hollow body, wherein the single overflap extends longitudinally out from one half or less of a perimeter of an edge of the adjoining end of the hollow body, wherein the single overflap includes two sides that taper towards each other as they extend from the edge of the adjoining end to a distal end of the single overflap, the distal end of the single overflap being parallel to the edge of the adjoining end of the hollow body, and wherein the single overflap is flexible and sized to at least partially extend around an exterior periphery of a non-end side of a recipient tissue and to position the non-end side of the recipient tissue adjacent to the adjoining end of the hollow body.

2. The tissue connector device according to claim 1, wherein the body comprises a biomaterial that is transparent, semi-transparent, or translucent.

3. The tissue connector device according to claim 1, wherein the tissue connector device comprises a biomaterial selected from the group consisting of: high-density polyethylene (HDPE), polyethylene glycol (PEG) hydrogel, purified proteins from human, animal, or synthetic sources, cellularized tissue constructs, and decellularized tissue constructs.

4. The tissue connector device according to claim 3, wherein the biomaterial is selected from the group consisting of: fibrin, demineralized bone, small intestine submucosa (SIS), dermis, collagen, muscle, fascia, and birth tissue.

5. The tissue connector device according to claim 4, wherein the biomaterial is amnion.

6. The tissue connector device according to claim 1, wherein the tissue connector device comprises a biomaterial, and wherein the biomaterial is decellularized and is demineralized bone, SIS, dermis, muscle, fascia, or amnion.

7. The tissue connector device according to claim 1, wherein the body comprises a biomaterial comprising porous HDPE or PEG surrounded by a layer of non-porous HDPE or PEG.

8. The tissue connector device according to claim 1, wherein the body comprises a biomaterial configured to allow passage of sutures therethrough.

9. The tissue connector device according to claim 1, wherein the body is a continuous tubular construct.

10. The tissue connector device according to claim 1, wherein the body is a non-continuous tubular construct of rolled material.

11. The tissue connector device according to claim 10, wherein layers of the rolled material are expandable to accommodate tissue positioned within the lumen.

12. The tissue connector device according to claim 1, wherein a diameter of the lumen at the adjoining end is approximately the same as a diameter of the lumen at the insertion end.

13. The tissue connector device according to claim 1, wherein a diameter of the lumen at the insertion end is greater than a diameter of the lumen at the adjoining end.

14. The tissue connector device according to claim 13, wherein the material around the insertion end is flexible and configured to be pulled, gathered, or crimped around the donor tissue when the donor tissue end is received in the insertion end.

15. The tissue connector device according to claim 1, wherein a diameter of the lumen is substantially consistent along a portion of a length of the body and then flares towards the insertion end.

16. The tissue connector device according to claim 15, wherein the diameter of the lumen is substantially consistent along at least one half of the length of the body.

17. The tissue connector device according to claim 1, wherein the diameter of the lumen is approximately 0.3 cm.

18. The tissue connector device according to claim 1, wherein the length of the body is approximately 0.75 cm to approximately 2.0 cm.

19. The tissue connector device according to claim 18, wherein the length of the body is approximately 1.0 cm.

20. The tissue connector device according to claim 1, wherein the distance by which the single overflap extends out from the adjoining end of the hollow body is approximately 0.2 cm to approximately 2.0 cm.

21. The tissue connector device according to claim 20, wherein the distance by which the single overflap extends out from the adjoining end of the hollow body is approximately 0.5 cm.

22. The tissue connector device according to claim 1, wherein the donor tissue and the recipient tissue are nerve tissue.

23. The tissue connector device according to claim 1, wherein a diameter of the lumen is approximately 0.25 cm to approximately 0.5 cm, and a length of the body is approximately 0.5 cm to approximately 3.0 cm.

24. The tissue connector device according to claim 1, wherein the single overflap extends out from the adjoining end of the hollow body a distance of approximately 0.1 cm to approximately 4.0 cm.

25. A tissue connector device for end-to-side connection of tissues, the connector device consisting of:
   a hollow body having an insertion end configured to receive a donor tissue end, an adjoining end, and a lumen therebetween; and
   a single overflap extending longitudinally out from the adjoining end of the hollow body, and integrally formed with the hollow body, wherein the single overflap is flexible and sized to at least partially extend around an exterior periphery of a non-end side of a recipient tissue and to position the non-end side of the recipient tissue adjacent to the adjoining end of the hollow body, wherein the tissue connector device comprises a biomaterial selected from the group consisting of: cellularized tissue constructs and decellularized tissue constructs.

26. The tissue connector device according to claim 25, wherein the body comprises a biomaterial that is transparent, semi-transparent, or translucent.

27. The tissue connector device according to claim 25, wherein the biomaterial is selected from the group consisting of: small intestine submucosa (SIS) and birth tissue.

28. The tissue connector device according to claim 27, wherein the biomaterial is amnion.

29. The tissue connector device according to claim 25, wherein the tissue connector device comprises a biomaterial, and wherein the biomaterial is decellularized and is demineralized bone, SIS, dermis, muscle, fascia, or amnion.

30. The tissue connector device according to claim 25, wherein the body comprises a biomaterial configured to allow passage of sutures therethrough.

31. The tissue connector device according to claim 25, wherein a diameter of the lumen at the adjoining end is approximately the same as a diameter of the lumen at the insertion end.

32. The tissue connector device according to claim 25, wherein the diameter of the lumen is approximately 0.3 cm.

33. The tissue connector device according to claim 25, wherein the distance by which the single overflap extends out from the adjoining end of the hollow body is approximately 0.5 cm.

34. The tissue connector device according to claim 25, wherein the donor tissue and the recipient tissue are nerve tissue.

35. The tissue connector device according to claim 25, wherein a diameter of the lumen is approximately 0.25 cm to approximately 0.5 cm, and a length of the body is approximately 0.5 cm to approximately 3.0 cm.

36. The tissue connector device according to claim 25, wherein the single overflap extends out from the adjoining end of the hollow body a distance of approximately 0.1 cm to approximately 4.0 cm.

\* \* \* \* \*